US008781755B2

(12) United States Patent
Wong

(10) Patent No.: US 8,781,755 B2
(45) Date of Patent: Jul. 15, 2014

(54) FUGITIVE EMISSION FLUX MEASUREMENT

(75) Inventor: Colin Irvin Wong, Burnaby (CA)

(73) Assignee: Golder Associates Ltd., Burnaby, BC (CA)

( * ) Notice: Subject to any disclaimer, the term of this patent is extended or adjusted under 35 U.S.C. 154(b) by 384 days.

(21) Appl. No.: 12/964,149

(22) Filed: Dec. 9, 2010

(65) Prior Publication Data

US 2011/0122397 A1 May 26, 2011

Related U.S. Application Data

(63) Continuation-in-part of application No. 12/575,854, filed on Oct. 8, 2009, now abandoned.

(60) Provisional application No. 61/136,837, filed on Oct. 8, 2008.

(30) Foreign Application Priority Data

Mar. 10, 2009 (CA) ...................................... 2655279

(51) Int. Cl.
| | | |
|---|---|---|
| *G01N 21/00* | (2006.01) | |
| *G01N 21/01* | (2006.01) | |
| *G01N 33/00* | (2006.01) | |
| *G01J 3/00* | (2006.01) | |

(52) U.S. Cl.
USPC .................. 702/22; 702/23; 702/26; 356/437

(58) Field of Classification Search
USPC ........ 702/22–24, 26, 32, 45, 49, 142; 356/51, 356/437; 73/31.05
See application file for complete search history.

(56) References Cited

U.S. PATENT DOCUMENTS

| 4,135,092 A | 1/1979 | Milly |
|---|---|---|
| 4,204,121 A | 5/1980 | Milly |

(Continued)

FOREIGN PATENT DOCUMENTS

| CA | 2219235 | 10/1997 |
|---|---|---|
| CA | 2550156 | 7/2005 |

(Continued)

OTHER PUBLICATIONS

Office Action issued Jun. 3, 2009 re counterpart application No. CA 2655279.

(Continued)

*Primary Examiner* — Michael Nghiem
*Assistant Examiner* — Alexander Satanovsky
(74) *Attorney, Agent, or Firm* — Gardner Groff Greenwald & Villanueva, P.C.

(57) ABSTRACT

A method of obtaining a fugitive emission flux measurement of airborne matter is provided. The method involves measuring the airborne matter along one or more than one measurement surface that spans the fugitive emission using two or more than two measurement beam paths where each of the two or more than two measurement beam paths are parallel to each other, or substantially parallel to each other, and determining a mass per unit length measurement for the measurement surface, determining a representative wind velocity at or near the one or more than one measurement surface, and calculating the fugitive emission flux of the airborne matter in mass per unit time using the mass per unit length determination and representative wind velocity.

16 Claims, 7 Drawing Sheets

(56) References Cited

U.S. PATENT DOCUMENTS

| | | | |
|---|---|---|---|
| 5,521,883 | A | 5/1996 | Fage et al. |
| 5,604,299 | A | 2/1997 | Cobb |
| 5,748,325 | A | 5/1998 | Tulip |
| 6,493,086 | B1 | 12/2002 | McAndrew et al. |
| 6,542,242 | B1 | 4/2003 | Yost et al. |
| 6,750,467 | B2 | 6/2004 | Tulip |
| 6,822,742 | B1 | 11/2004 | Kalayeh et al. |
| 6,864,983 | B2 | 3/2005 | Galle et al. |
| 6,995,846 | B2 | 2/2006 | Kalayeh et al. |
| 7,312,452 | B2 | 12/2007 | Klingenberg et al. |
| 7,375,814 | B2 | 5/2008 | Reichardt et al. |
| 7,523,638 | B2 | 4/2009 | Prince |
| 2010/0091267 | A1* | 4/2010 | Wong ............................... 356/51 |

FOREIGN PATENT DOCUMENTS

| | | |
|---|---|---|
| CA | 2675173 | 7/2008 |
| CA | 2655279 | 5/2009 |
| EP | 1972922 | 9/2008 |

OTHER PUBLICATIONS

Office Action issued Oct. 7, 2009 re counterpart application No. CA 2655279.
Office Action issued May 19, 2010 re counterpart application No. CA 2655279.
Scharff, H., "Landfill Gas Production and Emission on Former Landfill," Interreg IIIC report (on the internet), Oct. 2005.
Lamb et al., "Development of Atmospheric Tracer Methods to Measure Methane Emissions from Natural Gas Facilities and Urban Areas," Environmental Science & Technology, vol. 29, pp. 1468-1479, 1995.
Czepiel et al., "Landfill Methane Emissions Measured by Enclosure and Atmospheric Tracer Methods," J. Geophysical Research, vol. 101, No. D11, 1996.
Mount et al., "DOAS Measurement of Atmospheric Ammonia Emissions at a Dairy," 10th Annual Emission Inventory Conference, EPA, 2001.
Griffith et al., "Methane Emissions from Free-Ranging Cattle: Comparison of Tracer and Integrated Horizontal Flux Techniques," Journal of Environmental Quality, vol. 37, Issue 2, pp. 582-591, Mar./Apr. 2008.
Hensen & Scharff, "Methane Emission Estimates from Landfills Obtained with Dynamic Plume Measurements," Water, Air and Soil Pollution: Focus, vol. 1, No. 5-6, 455-464(10), 2001.
Huitric and Kong, "Measuring Landfill Gas Collection Efficiency Using Surface Methane Concentrations," SWANA 29th Annual LFG Symposium, St. Petersburg, Florida, Mar. 27-30, 2006.
Thoma et al., "Development of EPA OTM 10 for Landfill Applications Interim Report 2," Global Waste Management Symposium, Colorado, USA, Sep. 7-10, 2008.
Tregoures et al., "Comparisons of Seven Methods for Measuring Methane Flux at a Municipal Solid Waste Landfill Site," Waste Management & Research, 17, pp. 453-458, 1999.
Laubach and Kelliher, "Methane Emissions From Dairy Cows: Comparing Open-Path Laser Measurements to Profile-Based Techniques," Agricultural and Forest Meteorology, 135, pp. 340-345, 2005.
Weibring et al., "Remote Monitoring of Industrial Emissions by Combination of Lidar and Plume Velocity Measurements," Applied Physics B Lasers and Optics, 66, pp. 383-388, 1998.
Chambers, "Optical Measurements Technology for Fugitive Emissions from Upstream Oil and Gas Facilities," report prepared by Alberta Research Council Inc., Dec. 15, 2004.

Chambers et al., "DIAL Measurements of Fugitive Emissions from Natural Gas Plants and the Comparison with Emission Factor Estimates," 15th International Emission Inventory Conference, New Orleans, May 15-18, 2006.
United States Environmental Protection Agency, "Other Method 10 (OTM 10)—Optical Remote Sensing for Emission Characterization from Non-Point Sources," Jun. 14, 2006.
Babilott et al., "Fugitive Methane Emissions From Landfills: A field comparison of five methods on a French landfill," Global Waste Management Symposium, Colorado, USA, Sep. 7-10, 2008.
Van den Kroonenberg and Bange, "Turbulent flux calculation in the polar stable boundary layer: Multiresolution flux decomposition and wavelet analysis" Journal of Geophysical Research 112:, DO06112, doi:10.1029/2006JD007819, 2007.
Varma et al., 2004. "Optical Remote Sensing for Air Quality Monitoring," Poster BAQ Dec. 6-8, 2004 Agra India.
Thornton and Bomar, The Application of a Laser Based Open Path Spectrometer for the Measurement of Fugitive Emissions and Process Control. A&WM Association Conference Raleigh, North Carolina, Oct. 29, 1999.
Brown, "Remote Sensing Techniques in the Infrared Region of the Electromagnetic Spectrum," MSc Thesis May 2005.
Babilotte et al., "Field intercomparison of methods to measure fugitive methane emissions on landfills," Proceedings Sardinia 2009, 12th International Waste Management and Landfill Symposium S. Margherita de Pula Cagliari, Italy, Oct. 5-9, 2009.
Desjardins et al., "Evaluation of a micrometerological mass balance method employing an open-path laser for measuring methane emissions," Atmospheric Environment, 2004, 38:6855-6866.
Denmead, "Approaches to measuring fluxes of methane and nitrous oxide between landscapes and the atmosphere," Plant Soil, 2008, 309:5-24.
Milly, "The Vertical Grid Assessment of Air Pollution Sources," Int J Air Wat Poll, 1964, 8:291-295.
Oonk, Literature Review: Methane from Landfills: Methods to Quantify Generation, Oxidation and Emission. Apr. 2010. Report for Sustainable Landfill Foundation.
Gregory and Armstrong, "Review of Landfill Surface Emissions Monitoring DEFRA Report," Jun. 11, 2007, p. 74.
Gregory and Armstrong, "Review of Landfill Surface Emissions Monitoring," Global Waste Management Symposium, Sep. 7-10, 2008, Colorado, USA, p. 9.
Hashmonay and Yost, "Innovative Approach for Estimating Fugitive Gaseous Fluxes Using Computed Tomography and Remote Optical Sensing Techniques," Air & Waste Management Association, Aug. 1999, 49:966-972.
Office Action issued Jul. 2, 2010 re counterpart application No. CA 2655279.
Fugitive VOC—Emissions Measured at Oil Refineries in the Province of Vastra Gotaland in South West Sweden—a success story, developed and results 1986-2001, commissioned by the County of Vastra Goptaland, 2003.
Co-Pending U.S. Appl. No. 12/575,854, filed Oct. 8, 2009 entitled, Fugitive Emission Flux Measurement.
Office Action dated Feb. 7, 2011 for U.S. Appl. No. 12/575,854.
International Search Report dated Jan. 25, 2011 for international application No. PCT/CA2010/001614.
Office Action dated Feb. 1, 2011 for Canadian application No. 2,715,677.
Babilotte et al. "Fugitive Methane Emissions from Landfills: Field Comparison of Five Methods on a French Landfill", Journal of Environmental Engineering, 2010, pp. 777-784, ASCE.
Lenz et al. "Flights Testing of an Advanced Airborne Natural Gas Leak Detection System", ITT Industries Final Report, 2005, pp. 1-81.
Whiteman et al. "Raman Airborne Spectroscopic Lidar (RASL)—Final Report", 2002, pp. 1-42.
Thorneloe, "Evaluation of Fugitive Emissions Using Ground-Based Optical Remote Sensing Technology" EPA, 2007, pp. 1-76.

* cited by examiner

1ppm methane = 0.68mg/m³

FUGITIVE EMISSION FLUX MEASUREMENT

This application is a continuation-in-part of U.S. application Ser. No. 12/575,854, filed Oct. 8, 2009 (now abandoned), which claims priority upon Canadian Patent Application No. 2,655,279, filed Mar. 10, 2009, and U.S. Provisional Application No. 61/136,837, filed Oct. 8, 2008. The contents of these applications are incorporated herein by reference in their entireties.

FIELD OF INVENTION

The present invention relates to methods for obtaining a fugitive emission flux measurement of airborne matter.

BACKGROUND OF THE INVENTION

Fugitive emissions result from releases of airborne matter to the atmosphere from diffuse sources, which can include landfills, reservoirs, effluent ponds, mines, natural deposits, or even a collection of point-sources such as cities, industrial plants, or a herd of animals. Fugitive emissions can also include emissions from point sources, such as smokestacks, flares, wells, exhaust tubes, leaks and vent pipes, that have been released to the atmosphere. The airborne matters can be greenhouse gases, gaseous organic compounds, polluting gases, or particulate matter. The atmospheric volume within which the airborne matters exist is referred to as a plume and the emission flux is the flow rate of the airborne matter.

Flux boxes, dynamic closed chambers, and micrometeorological methods are point sampling techniques from which the emission flux from an area source must be extrapolated. Due to the extent and non-homogeneous nature of many area sources, assessment of fugitive emissions using traditional point sampling techniques can be problematic (Thoma, 2008). The accuracy of the flux box and dynamic closed chamber methods are dependent on the number of flux box or chamber tests conducted and provide an average flux over the sampling period. Use of flux boxes and dynamic closed chambers can also be time consuming and are not applicable to sources such as reservoirs or mines. Field tests for a large area can require many days to complete. If the fugitive emissions are dominated by one or more concentrated sources, such as cracks in a landfill, these methods may not be suitable.

Micrometeorological methods are applicable at locations that are uniformly flat and are a couple of hundred meters from the crest of a slope (Scharff, 2005). Thus the method is not applicable to many sites, which are sloping or have varying topography.

Atmospheric tracer methods involve releasing a tracer gas, often sulphur hexafluoride or nitrous oxide (potent greenhouse gases), or acetylene (Czepiel, 1996) into the emission plume. This method is restricted to situations where the source is sufficiently strong such that it can be measured at a sufficient distance downwind where adequate mixing of the airborne matter and tracer gas has occurred. As such, it is not suitable for confirmation of emissions from sites where emission rates are low (Czepiel, 1996). Measurement of flow of the tracer gas and physical sampling of the downwind air more than 100 m from the source is required (Czepiel, 1996; Griffith, 2008). Two to three different gas analyzers are required. For large area sources, such as cities, the method was reported to have an error as large as 65% for measured flux (Lamb, 1995).

The dynamic plume or inverse modelling method uses a fast response airborne matter detector to obtain concentration measurements in the plume, and then a dispersion model is used to estimate emissions (Hensen, 2001). A slight variant of this method is to use a flame ionization detector to obtain airborne matter concentrations just above the emission surface, and then to use an air dispersion model to calculate an emission rate (Huitric, 2006). The accuracy of the dynamic plume method is, in part, dependent on the accuracy of the dispersion model. Dispersion models can be complex and incorporate many simplifying assumptions.

Compared with point sampling techniques, optical remote sensing instruments have the advantage of sampling over a large volume, along an open path, and are able to provide continuous, real-time measurement of the integrated concentration of airborne matter. U.S. Pat. No. 6,542,242 teaches a method for mapping of airborne matter using path-integrated optical remote sensing (ORS) with a non-overlapping variable path beam length geometry (Radial Plume Mapping). Radial Plume Mapping uses optical remote sensing instruments to obtain path integrated data, that is processed reiteratively using a cumulative distribution function to provide a simplified map of the concentration of airborne matters. The assumed radial concentration pattern is determined based on an assumed cumulative density function. The method, in a vertical configuration, requires a ground-based, stable vertical structure on which to mount reflectors.

The United States Environmental Protection Agency's Other Test Method 10 (OTM 10) describes a method of applying the Radial Plume Mapping methodology in a vertical configuration for the measurement of fugitive emission flux. The method has been validated for application to relatively small, isolated area sources. Efforts to apply it to large area sources with complex topography are being attempted. However, this method may not sample the entire plume volume, as the height of the measurement path is limited by the angle from which the ground-based instrument is pivoted in order to target the highest vertical reflector (which is ground based). If the upper limit of the emission plume is higher than the highest measurement path, or the measurement beam paths do not bracket the emission plume, the accuracy of the method can significantly decrease as shown by the tracer release results in Thoma (2008).

The conventional mass balance method involves measuring the wind and airborne matter concentration profiles through the full height of the boundary layer containing emissions from the emitting source, and integrating the concentration and wind speed with respect to the height above ground surface. The method uses a ground-based mast (Tregoures, 1999) or a tethered balloon with a sampling sonde for point sampling of the air. The sampling balloon is held at different heights to obtain variations of concentration with elevation (Lamb, 1995). This point sampling method introduces an error since the whole region is not sampled.

U.S. Pat. No. 4,135,092 and U.S. Pat. No. 4,204,121 teach mass balance methods using either a number of point samplers mounted on a vertical pole or line, an aircraft flying through the plume at various elevations collecting samples at several height intervals, or vertically spaced infra-red radiation transmitters on a mast opposite another mast with a matching series of infra-red receptors. Sampling is only along horizontal lines and there is no teaching on the use of optical remote sensing instruments with targets or reflectors. Sampling can be made upwind of the source area to evaluate the contribution of incoming pollution to the apparent fugitive emission rate. However, it does not teach how to account for a natural background concentration of a pollutant in the atmosphere.

U.S. Pat. No. 6,864,983 teaches the use of a spectrometer for receiving absorption spectra from the sun, from which emission flux can be calculated. The method depends on the availability of direct sunlight and may only be used on sunny days. In addition, the accuracy of the method for some gases is questionable due to the long absorption distance through the atmosphere. For example, the significant background concentration of methane in the atmosphere results in a very large integrated concentration of methane, compared with the contribution of most methane emission plumes.

Mapping of airborne matters can also be carried out using Differential Absorption Laser Detection and Ranging (DIAL). It can be classified as a mass balance method that uses two Nd:YAG (neodymium-doped yttrium aluminum garnet; $Nd:Y_3Al_5O_{12}$) lasers. This equipment can map the concentration of airborne matters in the air, from which an emission flux can be calculated (Chambers, 2006). In an emission flux measurement application, this equipment is ground based, expensive, heavy and bulky.

U.S. Pat. No. 6,822,742 and U.S. Pat. No. 6,995,846 provide an airborne DIAL, using ND:YLF (neodymium-doped yttrium lithium fluoride; $Nd:YLiF_4$) lasers for detection of natural gas pipeline leaks, providing a path-integrated concentration of methane and ethane. Unlike the above method that uses two Nd:YAG lasers, this DIAL instrument does not map the concentration of airborne matter in the air. There is no teaching of measuring or quantifying emission flux of the gas leak.

A helicopter-borne spectroscopy method "Airborne Laser Methane Assessment" (ALMA) using a tunable diode laser (TDL) measures a path-integrated concentration in ppm-m on a vertical line. However, Babilotte (2008) state that ALMA "provides a path-integrated concentration on a vertical line, and does not allow fluxes quantification".

All of the above methods either have significant constraints that limit their applicability and accuracy, or are tools for which a methodology to measure fugitive emission fluxes is not available. What is needed is a method that can obtain data within a reasonable time frame, can carry out measurements throughout the entire thickness and width of the emission plume, thereby improving accuracy, does not involve very limited point sampling of airborne matter concentrations, does not require infra-red transmitters to be opposite infra-red receivers, and is suitable for application to emission sources over a large area or of a plume height that extends above ground-based moveable platforms. Furthermore, the method may not require access more than 100 m downwind of a source, does not require complex numerical modelling of airborne matter dispersion or mapping of airborne matter concentrations, and does not require specific release of a tracer gas.

SUMMARY OF THE INVENTION

The present invention relates to methods for obtaining a fugitive emission flux measurement of airborne matter.

It is an object of the invention to provide an improved method for measurement of fugitive emission flux.

The present invention provides a method (A) of obtaining a fugitive emission flux measurement of airborne matter within a fugitive emission from an emission source of interest, comprising:

a) measuring the airborne matter using an airborne platform comprising an optical remote sensing instrument (ORSI) and one or more than one ground-based target along one or more than one measurement surface using two or more than two measurement beam paths, where each of the two or more than two measurement beam paths are vertical or substantially vertical, and parallel to each other, or substantially parallel to each other, the one or more than one measurement surface is of a height and width that spans or substantially spans the fugitive emission, and is oriented along a transverse straight path, or along a curved path, relative to a wind direction, and determining a parts per million meter (ppm-m) or a mass per unit area measurement of the airborne matter for each of the two or more than two measurement beam paths, the height being a distance between the ORSI on the airborne platform and the ground-based target;

b) determining a wind velocity at one or more locations at or near each of the one or more than one measurement surface to obtain a representative wind velocity;

c) integrating, with respect to a component of a length along the one or more than one measurement surface that is perpendicular to the wind direction and transverse to a direction of the two or more than two measurement beam paths, the parts per million meter (ppm-m) or mass per unit area measurement of the airborne matter obtained from each of the two or more than two measurement beam paths, and determining a total mass per unit length of the airborne matter for each of the one or more than one measurement surface; and d) calculating the fugitive emission flux of the airborne matter in mass per unit time using a total mass per unit length of the airborne matter and the representative wind velocity.

The present invention further provides a method (B) of obtaining a fugitive emission flux measurement of airborne matter within a fugitive emission from an emission source of interest, comprising:

a) measuring the airborne matter using a ground-based platform comprising an optical remote sensing instrument (ORSI) and an airborne target along one or more than one measurement surface using two or more than two measurement beam paths, where each of the two or more than two measurement beam paths are vertical or substantially vertical, and parallel to each other, or substantially parallel to each other, the one or more than one measurement surface is of a height and width that spans or substantially spans the fugitive emission, and is oriented along a transverse straight path, or along a curved path, relative to a wind direction, and determining a parts per million meter (ppm-m) or a mass per unit area measurement of the airborne matter for each of the two or more than two measurement beam paths, the height being the distance between the ORSI on the ground-based platform and the airborne target;

b) determining a wind velocity at one or more locations at or near each of the one or more than one measurement surface to obtain a representative wind velocity;

c) integrating, with respect to a component of a length along the measurement surface that is perpendicular to the wind direction and transverse to a direction of the to the two or more than two measurement beam paths, the parts per million meter (ppm-m) or mass per unit area measurement of the airborne matter obtained from each of the two or more than two measurement beam paths, and determining a total mass per unit length of the airborne matter for each of the one or more than one measurement surface; and d) calculating the fugitive emission flux of the airborne matter in mass per unit time using a total mass per unit length of the airborne matter and the representative wind velocity.

The present invention also provides the methods (A) or (B) as described above, further comprising a step of correcting for a background concentration of airborne matter or a flux from an upwind emission source by:

i. determining the background concentration and using this measurement and the measurement of airborne matter from each of the two or more than two beam paths, to obtain a corrected measurement of the airborne matter as measured in step (a), or ii. correcting the fugitive emission flux determined in (d) by using steps (a) to (d) to determine a flux of airborne matter upwind of the emission source of interest.

The background concentration can be determined by dividing the parts per million meter (ppm-m) or a mass per unit area measurement obtained in a background area by a distance between the ORSI and the target to obtain a concentration of airborne matter as mass per unit volume or ppm, or by determining an upwind flux obtained by applying steps (a) to (d) upwind of the emission source of interest.

The present invention provides the method (A) or (B) as described above wherein the airborne matter in step (a) may be measured using open-path optical remote sensing methods such as tunable diode laser (TDL) absorption spectroscopy, differential absorption laser detection and ranging (DIAL), open path Fourier transform infrared (OP-FTIR) spectroscopy, differential optical absorption spectroscopy (DOAS), Raman spectroscopy, backscatter absorption gas imaging (BAGI), or any other open path measurement technique as would be known to one of skill in the art. The wind velocity in step (b) may be obtained with an anemometer or sodar.

Furthermore, the amount of airborne matter along a top of the measurement surface may be measured.

The present invention also includes a computer readable memory having recorded thereon statements and instructions for execution by a computer to carry out the method (A) or (B) as described above.

A measurement beam path sampled by an optical remote sensing instrument (ORSI), according to the methods described herein may extend vertically, or substantially vertically, from the ground to the upper limit, or beyond, of the emission plume. The ORSI may be ground-based (e.g. on a fixed or mobile platform) or may be mounted on an airborne platform. The measurement beam is directed, along a measurement beam path, to a target that reflects the measurement beam to a detector that is typically part of the ORSI. For example, the target may be mounted on an airborne platform, for use with a ground-based ORSI, or the target may be ground-based, and the ORSI located on an airborne platform. Alternately an airborne platform mounted ORSI may use the ground as a target to reflect the measurement beam. This arrangement can provide for a measurement beam path that passes vertically or substantially vertically, through the entire height, and width (as determined by the measurement beam path selected) of the emission plume. Two or more measurement beam paths can be used to determine a measurement of the mass per unit length of airborne matter within a measurement surface.

The flight path of the airborne platform and travel path of the ground-based mobile platform are parallel or substantially parallel, and the measurement beam emitted from the ORSI, or reflected from the target and received by the detector, are vertical, or substantially vertical and span the distance between the airborne platform and ground-based platform, intersecting the emission plume.

Measurement occurs along successive distinct parallel or substantially parallel measurement beam paths, and if desired, along distinct sampling surfaces. This sampling method ensures that localized areas of higher pollutant concentration are not repeatedly sampled, as could be the case if, for example the measurement paths are radial or substantially non-parallel. The methods described herein is more accurate than that of methods that have a measurement beam that extends only partway through the emission plume, such as for example OTM 10, of a large and tall landfill, since the methods described herein do not require extensive extrapolation. In the methods described herein, the measurement beam path describes a vertical, or substantially vertical measurement plane as the airborne or ground-based mobile platform follows a measurement beam (travel) path, or measurement surface, across the emission plume. In the case of an airborne ORSI, the travel path can be set to be above the height of the plume, to ensure that each measurement beam path along the measurement surface passes through the depth (from the top to the ground) of the plume. The travel path may be straight, approximately straight, or curved. The mass per unit length of airborne material within the measurement surface through which multiple optical path measurements (along a measurement beam path) are obtained describes a cross section of the emission plume. The wind velocity may also be also determined for each measurement surface. The data obtained for the measurement surface is processed by an algorithm, and the calculated mass per unit length and wind velocity are used to calculate a flux of the fugitive emission. The algorithm used to process the data does not require reiterative calculation of a cumulative distribution function to provide a map of the concentration of airborne matter.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE DRAWINGS

These and other features of the invention will become more apparent from the following description in which reference is made to the appended drawings wherein.

DETAILED DESCRIPTION

Figure 1:
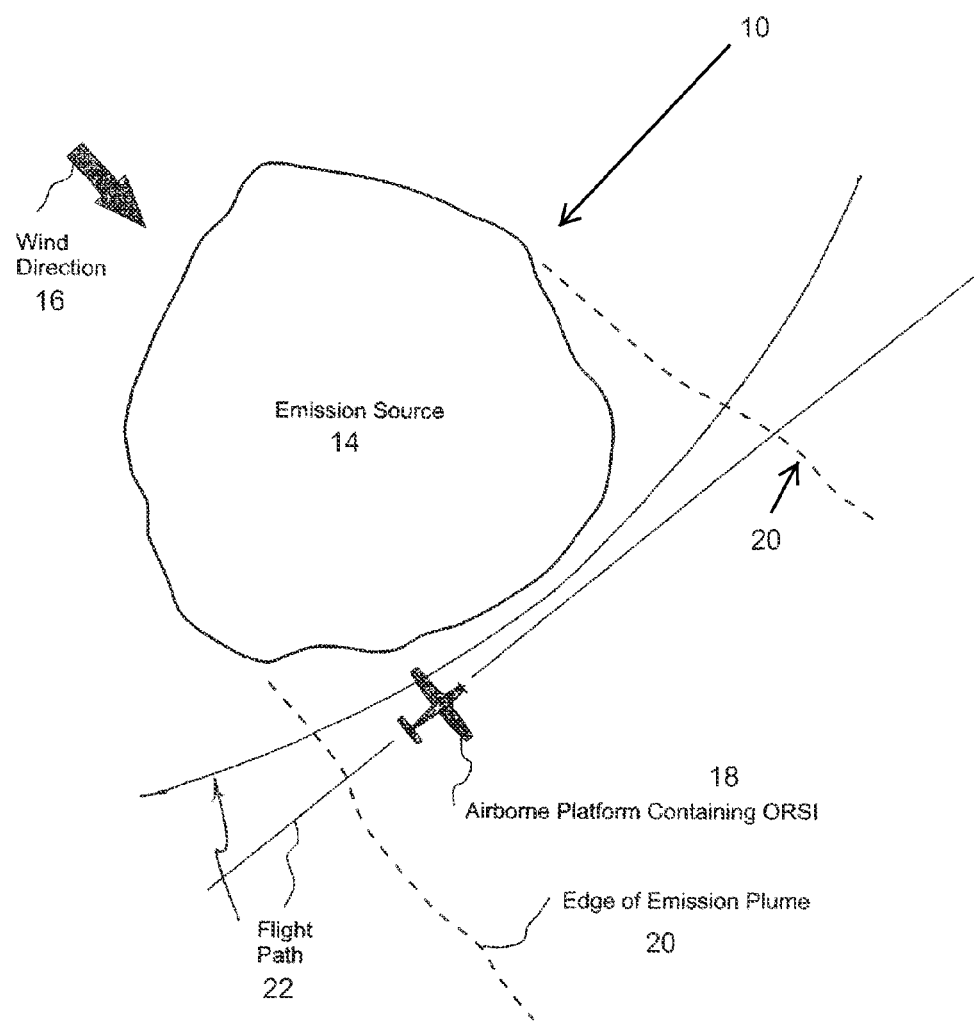
FIG. 1 shows a plan view of a first mode (airborne based ORSI), showing an emission source, an airborne platform and two flight paths transverse to the wind direction.

The present invention relates to methods for obtaining a fugitive emission flux measurement of airborne matter.

The following description is of a preferred embodiment.

The present invention provides a method (Total Plume method) of obtaining a fugitive emission flux measurement of airborne matter from an emission source of interest. The method involves measuring the airborne matter using an optical remote sensing instrument (ORSI) along one or more than one measurement surface using two or more than two measurement beam paths, where each of the two or more than two measurement beam paths are parallel to each other, or substantially parallel to each other, and determining a parts per million meter (ppm-m) or a mass per unit area measurement of the airborne matter. The one or more than one measurement surface is of a height and width that spans or substantially spans the fugitive emission, and is oriented along a transverse straight path, or along a curved path, relative to a wind direction. Wind direction is defined herein as the direction of travel of a weightless particle suspended in the wind. A wind velocity is measured at one or more locations at or near each of the one or more than one measurement surface to obtain a representative wind velocity. A total mass per unit length of the airborne matter for each of the one or more than one measurement surface is calculated by integrating the parts per million meter (ppm-m) or mass per unit area measurement of the airborne matter obtained from each of the two or more than two measurement beam paths, with respect to a component of the measurement surface, that is perpendicular, or substantially perpendicular, to the wind direction and transverse to the measurement beam direction. For example, assume y is the direction of the wind, z is the vertical direction, and x is perpendicular to the y and z directions, and that a measurement surface is a function of y and x. The component of the measurement surface that is perpendicular to the wind direction and transverse to the measurement beam direction would be in the x direction. The fugitive emission flux of the airborne matter (in mass per unit time) is calculated as a product of the total mass per unit length of the airborne matter and the representative wind velocity.

Examples of airborne matter from an emission source of interest include, but are not limited to compounds, molecules, one or more than one gas of a single species or a mixture of two or more gasses for example but not limited to greenhouse gasses for example but not limited to carbon dioxide, methane, nitrous oxide, and the like, gaseous organic compounds for example combustible gasses, natural gas, methane, ethane, propane, or emissions from petrochemical plants, polluting gasses for example, sulphur dioxide, ammonia, ozone, vehicle emissions, emissions from landfills, industrial emissions, radioactive emissions, toxic emissions, particulate material and the like. Airborne matter may also be referred to as a subject gas.

Figure 2:
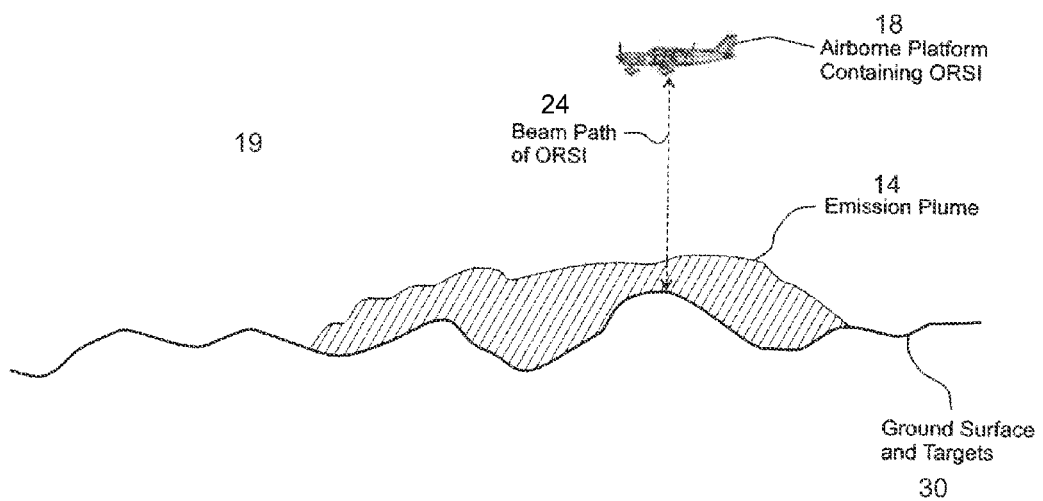
FIG. 2 shows a profile view of the plan view of FIG. 1, showing an airborne based ORSI: an airborne platform containing the ORSI above an emission plume, and a measurement beam path of the ORSI.

Referring to FIGS. 1 and 2, a non-limiting example of the invention is shown generally at 10. An airborne platform 18 upon which an optical remote sensing instrument (ORSI) is mounted, flies above, or substantially above, an emission plume 20 caused by the emission source 14, and surrounding airspace 19, to obtain measurements. The airborne platform flies along a flight path 22 that is above the plume 20 that defines a measurement surface. The flight path is transverse to a wind direction 16, and may be along a traverse straight path, or along a curved path, relative to a wind direction 16 (see FIG. 1). A transverse flight path may be from about 170 to about 10 degrees from the wind direction, or any amount therebetween (i.e. not parallel to the wind direction), for example 10, 20, 30, 40, 50, 60, 70, 80, 90, 100, 120, 130, 140, 150, 160, 170 degrees from the wind direction, or any amount therebetween.

If the surface, or portion thereof, formed by the measurement beam paths is not perpendicular to the wind direction, then each measurement value determined along each of the beam paths (path-integrated concentration in ppm-m or mass per unit area) can be projected in the wind direction onto an imaginary plane (a measurement plane) that is oriented perpendicular to the wind direction, and the ppm-m or the mass per unit are measurement of the airborne matter determined.

The flight path, or measurement surface, 22 may extend beyond the edges of the emission plume 20. The height of the flight path above the plume is selected such that the ORSI is above, or substantially above, the plume, for example, so that from about 90% to 100%, or any amount therebetween of the emission mass per unit length, for example 90, 95 or 100% or any amount therebetween of the emission mass per unit length, is within the measurement surface. In this way the mass per unit length of airborne material in a cross-section of the plume, in the Total Plume method as described herein, may be accurately determined. The flight path 22 defines a measurement surface along which one or more than one measurement, may be made along a measurement path 24 (or measurement beam path) between the airborne platform 18 and the ground 30.

As an option to confirm that the flight path is above or substantially above the plume, the airborne platform may be equipped with an ORSI or another instrument (such as a point sampling instrument, for example a flame ionization detector) that can sample the air that the airborne platform travels through. The ORSI used for the measurement beam through the plume could also be used if it is configured to obtain measurement of both the plume and the top of the measurement plane, for example by multi-plexing. If these air measurements indicate concentrations of airborne matter that are at or within about 0.1 to 0.001 ppm or any amount therebetween, of background concentrations, depending on the airborne matter, this indicates that the top of the measurement surface is above, or substantially above, the plume.

Alternatively, the airborne platform can make two or more flight paths along the same measurement surface, with each flight path at a different elevation. The flight path at the lowest elevation would be above or substantially above the plume if the difference between the emission flux determined by the lowest elevation flight path is essentially the same as the flux determined by a higher flight path. However, this method can be influenced by temporal variations in wind velocity and emission plume concentration distribution and is therefore not a preferred method of confirming that the lower elevation flight path is above or substantially above the plume.

For relatively small sources, and if the ORSI can provide measurement beams that can span or substantially span the emission plume the flight path may be parallel to the emission plume. However a measurement surface that is perpendicular to the wind direction would be selected to calculate the emission flux.

The measurement beam path, also referred to as a measurement path 24, of the ORSI may be directed from the airborne platform 18 to a ground surface or a target at the ground surface 30. For increased accuracy, the measurement beam path 24 may be perpendicular or substantially perpendicular to the wind direction 16. Normally for horizontally flat ground, this means that the measurement beam path 24 is vertical or substantially vertical, for example varying from about 0-30 degrees, or any amount therebetween from vertical for example 0, 2, 4, 6, 8, 10, 12, 14, 16, 18, 20, 22, 24, 26, 28, 30 degrees from vertical. If more than one measurement is obtained along the measurement surface 22, for example if two or more than two measurement paths are used, then each of the measurement paths 24 are parallel, or substantially parallel with respect to each other.

The method will have increased accuracy if the measurement beam paths are parallel. However, this is not always achievable in practice. The measurement beam paths may therefore be substantially parallel, and preferably, for example from about 0 to about 15 degrees from parallel or any amount therebetween, for example 0, 2, 4, 6, 8, 10, 12, 14, and 15 degrees or any amount therebetween, from parallel. Preferably, for increased accuracy, each of the two or more than two measurement beam paths are non-intersecting. In this way separate discrete measurement beam paths 24 through a plume are carried out. As the airborne platform traverses the area encompassing and surrounding the emission plume, a series of measurement beam paths 24 of one or more than one wavelength are emitted by the ORSI, reflected off, in this example, the ground surface or target 30, and the reflected measurement beam is detected by the ORSI.

Figure 3:
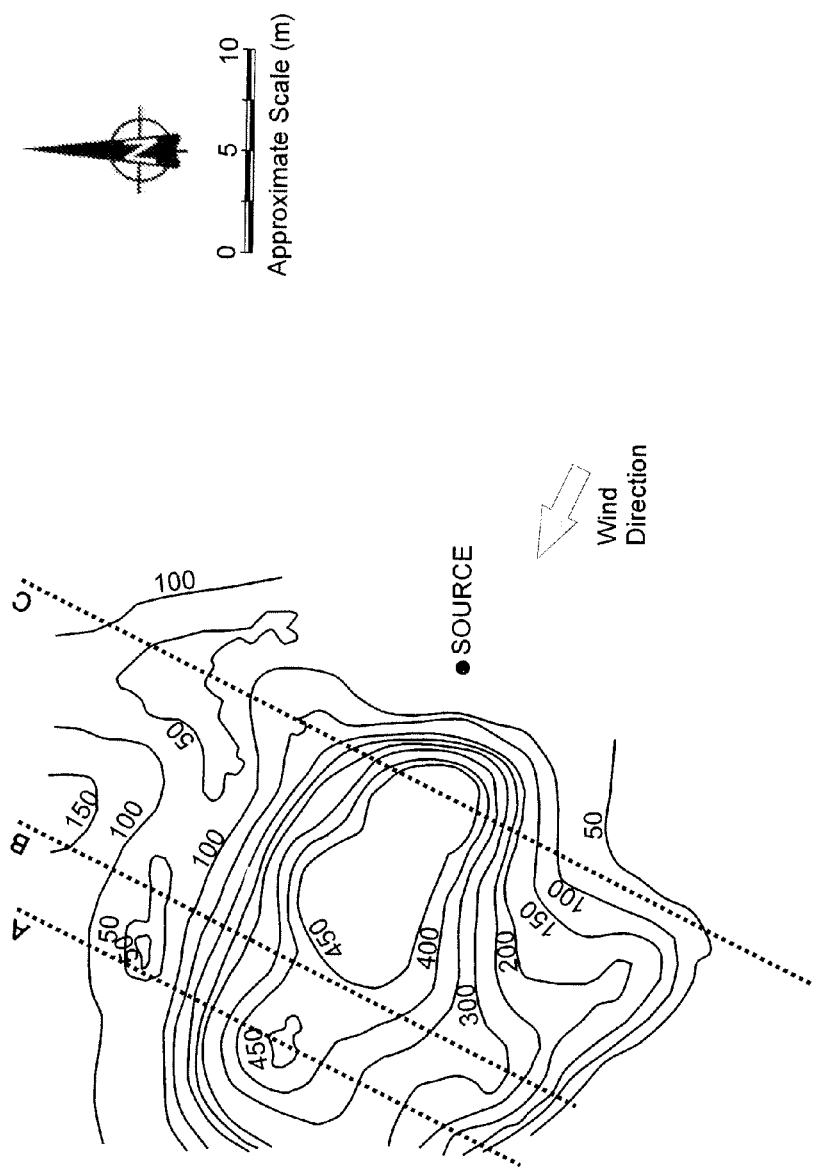
FIG. 3 shows a plan view of a site with an emission plume; the contours (integrated concentration in ppm-m) of regions of airborne matter in the plume are shown on the view. Measurement planes A, B, C are indicated by dotted lines intersecting the plume substantially perpendicular to the wind direction.
Figure 4:
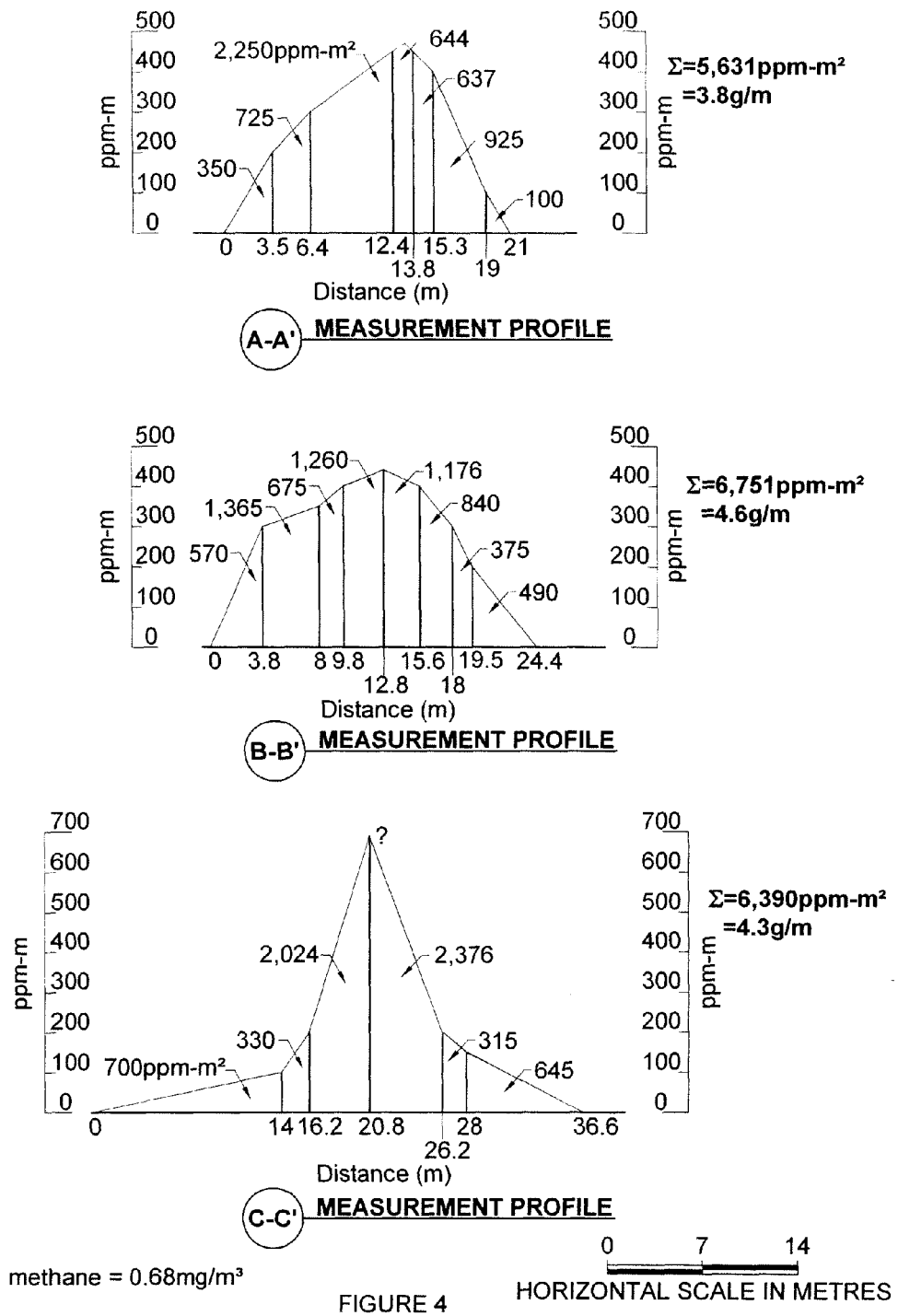
FIG. 4 shows the measurement results from three measurement surfaces obtained along flight paths A, B and C. The horizontal axis is the width along the horizontal component of the measurement surface that is perpendicular to the wind direction. The vertical scale is the measurement value for each measurement beam in ppm-m.

In the Total Plume as described herein, the measurement surface 22 may extend beyond the sides of the plume. Furthermore, more than one flight path, or measurement surface 22 may be executed, so that a series of measurement surfaces 22 are defined through the plume 20. The flight path may be straight or curved and may vary in elevation. FIG. 3 illustrates a non-limiting example, comprising three flight paths (A, B, C) across a plume, with each flight path at a different horizontal distance from an emission source (source). FIG. 4 illustrates results obtained from data collected from measurement planes A, B, C. Each measurement surface A, B, C comprises measurement beam paths that are indicated as vertical lines. The area under the curve of each of the measurement surface is the mass per unit length of the airborne matter.

Figure 5:
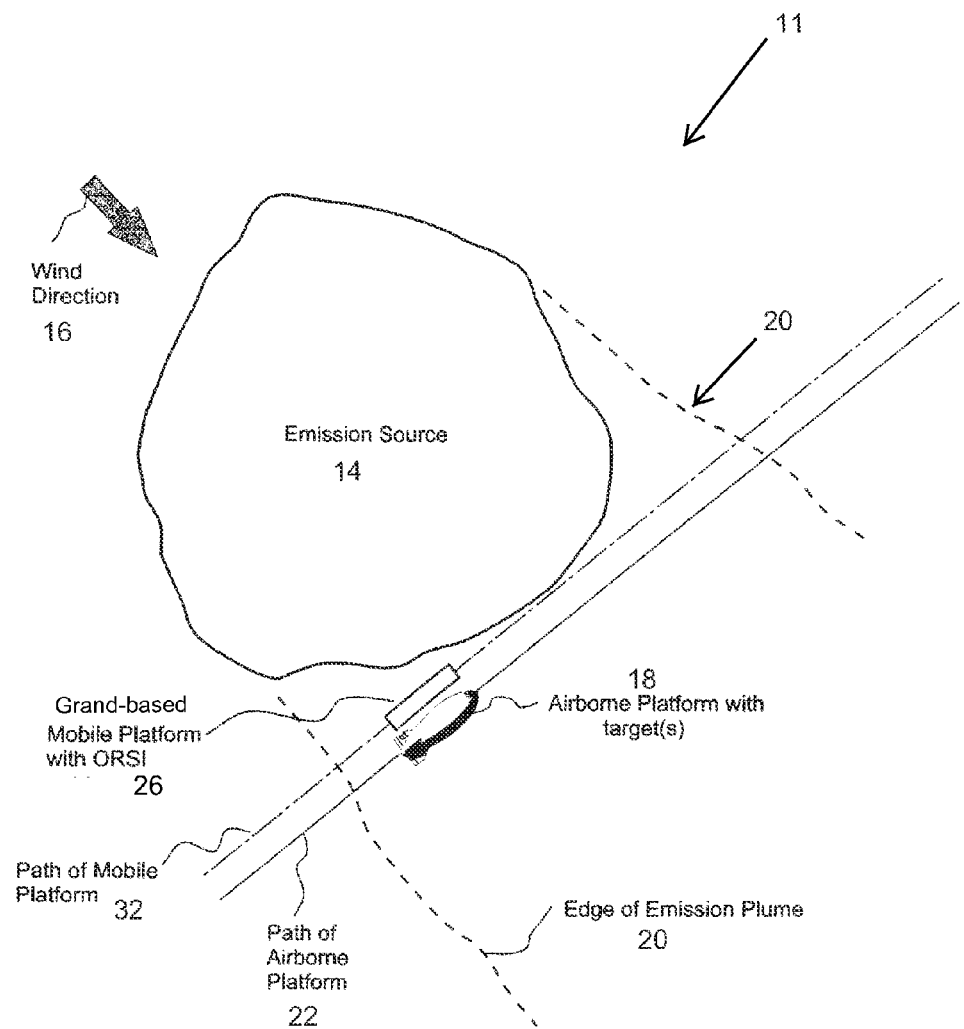
FIG. 5 shows a plan view of a second mode (ground based mobile ORSI), showing an emission source, a mobile platform on which the ORSI is mounted, an airborne platform comprising a target (the airborne platform may have a mounted target, or itself be the target), and their respective travel paths.

Referring to FIG. 5, another example of the invention is shown generally at 11. A ground-based mobile platform 26 (e.g. a vehicle or trailer) upon which an ORSI is mounted, follows a path 32 on the ground that is transverse to a wind direction 16. An airborne platform 18 comprising a target (e.g. with a retroreflector) travels along a flight path 22 that is above or substantially above the emission plume 20 and from about 0, 1, 2, 3, 4, 5, 6, 8, 10, 12 and 15 degrees, or any amount therebetween, from parallel to the path 32 of the ground-based mobile platform 26. The paths of the ground based and airborne platforms may be downwind of the emission source, as illustrated in FIG. 5, for example transverse to the wind direction, or about +/−80 degrees or any amount therebetween as measured from a direction that is perpendicular to the wind direction, for example 2, 4, 6, 8, 10, 15, 20, 25, 30, 35, 40, 45, 50, 55, 60, 65, 70, 75 and 80 degrees or any amount therebetween as measured from the wind direction. The measurement surface defined by the path of the airborne platform 22 and the path of the ground based platform 32, extends beyond the edges of the emission plume 20 and may be straight or curved.

If the surface, or portion thereof, formed by the measurement beam paths is not perpendicular to the wind direction, then each measurement value determined along each of the beam paths (path-integrated concentration in ppm-m or mass per unit area) can be projected in the wind direction onto an imaginary plane (a measurement plane) that is oriented perpendicular to the wind direction, and the ppm-m or the mass per unit are measurement of the airborne matter determined.

Figure 6:
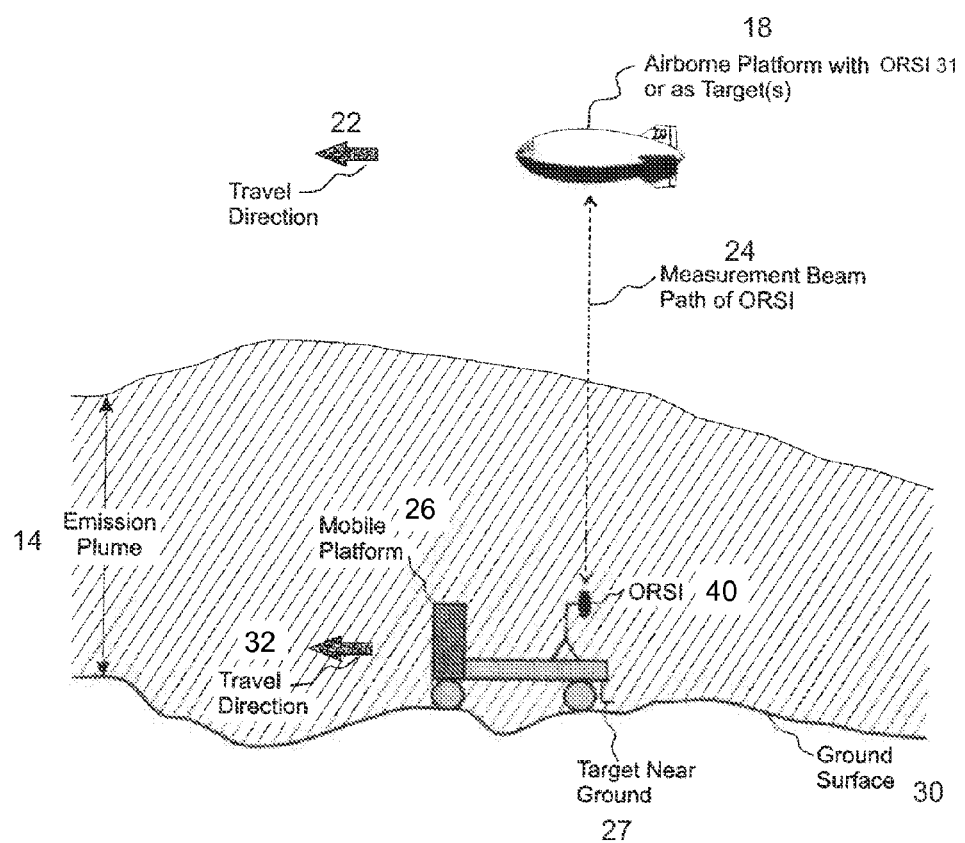
FIG. 6 shows a profile view of the plan view of FIG. 5, showing a mobile, ground based ORSI, the ORSI, and a measurement beam path of the ORSI.

Referring to FIG. 6, a measurement beam 24 of an ORSI (40) is directed to one or more than one target on the airborne platform 18; the measurement beam path 24 may be vertical, or substantially vertical, for example varying from about 0-30 degrees, or any amount therebetween from vertical for example 0, 2, 4, 6, 8, 10, 12, 14, 16, 18, 20, 22, 24, 26, 28, 30 degrees from vertical. As the mobile platform 26 traverses the area to be surveyed, a series of measurement beam paths 24 of one or more wavelengths are emitted by the ORSI (40), reflected off the one or more targets of the airborne platform 18 and the reflected measurement beam received by the ORSI. If more than one measurement is obtained along the measurement surface 22/32, then each of the measurement paths 24 are parallel, or substantially parallel, for example varying from about 0-15 degrees from parallel or any amount therebetween, for example 0, 2, 4, 6, 8, 10, 12, 14, 15 degrees from parallel. The plurality of measurement paths 24, generally describe a measurement surface 22/32 in cross section to the plume 20 and surrounding airspace 19 (as shown in FIGS. 5 and 6).

As described above, the measurement beam path may be directed or oriented such that a series of measurements obtained using the ORSI provides a measurement surface that is vertical or substantially vertical.

To account for a background concentration of airborne material, it is necessary to also measure the length of all the measurement beams both within the emission plume and in a background area. This length can be determined by any number of methods to one of skill in the art. Height from the ground or target surface to the ORSI on the airborne platform may be determined using an altimeter, laser rangefinder, radar, or other distance measuring device as would be know to one of skill in the art.

Operation and Equipment

The fugitive emission flux of airborne matter at a site may be obtained as follows:
  i) determine the site to be profiled;
  ii) determine the airborne material, gas, matter, or a combination thereof to be measured;
  iii) determine the representative wind velocity (direction and speed);
  iv) determine a measurement surface that is along a transverse straight path, or a curved path, relative to the wind direction;
  v) select an ORSI with a suitable electromagnetic wavelength or wavelengths (for example, if multiple species of airborne material are to be measured) to be used to measure the path integrated concentration (ppm-m or mass per unit area) of airborne matter;
  vi) using the ORSI, obtain one or more than one measurement of the mass per unit area of the airborne matter in a measurement beam path located within the selected measurement surface;
  vii) using the values determined for each of the one or more than one measurement beam path, determine the amount of airborne matter along the measurement surface to obtain the mass per unit length of the airborne matter within the measurement surface; and viii) using the mass per unit length of airborne matter within the measurement surface and representative wind velocity, calculate the emission flux of the airborne matter in mass per unit time.

Optical remote sensing instrumentation (ORSI) apparatus employed in step (v) above, and for the methods, apparatus and systems according to various embodiments of the invention as described herein refers to an open-path measurement apparatus whose measurement beam can be aimed in a particular direction, or directed to a specific target or series of targets. An apparatus that measures path-integrated concentration of one or more than one species of airborne matter across an open path of air may be generally referred to as an open-path measurement apparatus.

The ORSI provides data output in the form of a measurement in mass of airborne matter per unit area along the measurement beam path, or a path integrated concentration (typically in parts per million-meter or ppm-m, but can be in any other equivalent units). A ppm-m measurement can readily be converted to mass per unit area by multiplying the ppm-m measurement by the appropriate conversion factor for the particular airborne matter at the air temperature and air pressure at the time of the measurements. A similar calculation can be carried out if different units (other than ppm and ppm-m) are used. Alternatively, the mass of airborne matter per unit area may be reported directly by the ORSI.

The ORSI may comprise tunable diode laser (TDL) instruments, for example manufactured by Boreal Laser Inc., differential absorption laser detection and ranging (DIAL) instruments for example as supplied by ITT ANGEL Service, open path Fourier transform infrared (OP-FTIR) spectroscopy instruments for example manufactured by Edo Corporation, or differential optical absorption spectroscopy (DOAS) instruments for example manufactured by Opsis Inc. Other methods, such as Raman spectroscopy or backscatter absorption gas imaging (BAGI), or any other open path measurement technique as would be known to one of skill in the art, may also comprise the ORSI.

The measurement beam produced by the ORSI may be provided by, for example but not limited to, one or more lasers of one or more wavelengths, or a light or electromagnetic radiation source (EMR) of one or more wavelengths, including at least one wavelength that is absorbed by a gas or particulate of interest. The measurement beam is of a brightness that meets the requirements of the methods taught herein. For example such light or EMR sources could include a laser, a tunable diode laser, a laser followed by a frequency conversion device, an incandescent light, an EMR source passing through an appropriate filter, or an LED source. The light or EMR source is capable of emitting at a single-wavelength or multiple wavelengths as required. In addition, the beam generated by the light, EMR, or laser is intended to include wavelengths that are efficiently propagated across the measurement path, and includes electromagnetic radiation in the ultraviolet, visible, near infrared, or infrared portions of the spectra, as appropriate. If desired, alternate sources, for example thermal, ultrasound, radio waves, microwaves, or X-rays may also be used for a measurement beam, as required.

The ORSI further comprises one or more than one detector to receive a portion of the measurement beam that is reflected back to the ORSI by one or more targets. The detectors may include multiple detectors, or an array of detectors, and the detector can be remote from the unit housing the measurement beam source. The data so obtained is stored by a data logging apparatus, such as computer readable memory, or processed using an algorithm with a central processing unit (CPU).

The one or more than one detector is generally a photon detector, however if appropriate thermal detectors, or detectors that measure ultrasound may also be used. A detector is selected to be compatible with the one or more than one measurement beam employed. For example, on ORSI and detector may be designed to detect methane using the mid to near infrared range (wavelengths of 0.7-8 microns), while determining other airborne matter or subject gas concentration, for example benzene concentration, a detection beam containing wavelengths in the ultraviolet range may be useful (wavelengths of 0.01 to 0.40 microns).

The measurement beam path of the ORSI is directed through the emission plume, to one or more than one targets. A target is a surface or device that reflects the measurement beam of the ORSI, or its backscatter, back to the detector of the ORSI. Examples of targets include, but are not limited to, retroreflectors, a reflective surface, vegetation, ground, airborne platforms, mobile platforms, vehicles, bodies of water, structures, or the like. If the vegetation, ground, or structures are used as targets, a correction for different reflectivity or absorption intensities may need to be applied to the measurements. This effect can be estimated by measurement in an area with background concentrations of the airborne matter against material of the same reflectivity as along the measurement paths for the emission plume.

The length of each measurement beam path is measured. This is also required when it is desired to correct for a background concentration of an airborne material. The location and relative elevation of the ORSI and targets may be determined by any of various methods known in the art, for example including Global Positioning System (GPS), altimeter, measurement tape, surveying methods, topographic maps, laser rangefinders, or the like. Optionally, the elevation of the ground surface along a measurement path may also be determined. The elevation may be relative to sea level, or relative to an airborne platform. The distance between the ORSI and the target may be determined by the altitude of the airborne platform, or by a laser rangefinder, or the time required for the measurement beam reflected by the target to reach the detector, or a physical measurement between the ORSI and target for example.

It may also be useful to record the air temperature and pressure at the time of measurement so that the appropriate conversion of ppm to mass per unit volume can be applied. The air pressure can also be estimated from the elevation of the emission plume Background concentration of the airborne matter in air is considered to be the concentration of the airborne matter in the atmosphere in the absence of emission sources and may be determined by measuring the concentration of airborne matter in the atmosphere in the absence of emission sources. The background concentration can be obtained by dividing the ORSI measurement beam value (ppm-m or mass per unit area) in a background area by the distance between the ORSI and the target to obtain ppm or mass per unit volume.

If there is another emission source upwind of the emission source of interest, then the flux from the upwind emission source also needs to be determined so that it can be subtracted from the total emission flux downwind of the emission source of interest. In examples where the background concentration of the airborne matter is considered to be zero, or substantially zero, the step of adjusting for the background concentration may be omitted.

The transmitter and detector of the ORSI may be integrated into or adjacent to the instrumentation. In another embodiment, the ORSI may be in communication with a long-path transmitter and detector head, via communication means such as fiber optic cable, wire, or electromagnetic transmitter and receiver; the long-path transmitter and detector head may be movable independently of the ORSI. The portable long-path transmitter/detector head may be manually directed at a target. In an alternate embodiment, any of several multiplexing techniques may be employed such that a single ORSI instrument can monitor several targets at the same time. Techniques that are known in the art, for example but not limited to, wavelength division multiplexing (WDM) and time division multiplexing (TDM) may be used.

One or more wind velocity measurement devices may be used to measure the wind speed and direction at a location or locations that are representative of the wind velocity across the measurement surface. The wind velocity measurement devices can be local measurement instruments, such as anemometers, or remote measurement instruments such as sonic detection and ranging (Sodar) instrumentation (see, for example, U.S. Pat. No. 5,521,883). In some embodiments, the wind velocity and ORSI data may be recorded and logged in a time-synchronous manner. Alternately, the wind velocity data and ORSI data may be recorded independently by the same datalogging device, or by two or more separate datalogging devices, and the recorded data time-stamped to allow for correlation of wind velocity with ORSI data at a later point. In some embodiments, more than one wind velocity measurement device can be used and/or the wind measurement data can be input into an emissions dispersion or wind velocity model to derive a representative wind velocity at the measurement plane. Use of a plurality of wind velocity measurement devices may be useful for large emission plumes.

The airborne platform can be a manned or unmanned or remote-controlled airplane, glider, helicopter, balloon, kite, dirigible or the like. The position of the airborne platform should be controllable by a user to allow for positioning and measurement, but does not need to be in a fixed position while data or measurements are obtained. In some embodiments, the airborne platform houses the ORSI; in other embodiments, the airborne platform houses one or more targets, or is itself a target (i.e. an airborne structure).

A mobile platform is typically a ground based vehicle on which an ORSI can be mounted. As an option, an ORSI can be connected, by fibre optic cable, to a portable long-path transmitter and receiver head. The portable long-path transmitter/receiver head can be manually pointed at a target. The mobile platform may also have an attached target near to the ground, to enable measurement of airborne matter integrated concentrations between an airborne ORSI device and the ground.

Movement of the ORSI may increase the difficulty in obtaining consistent measurements due to motion of the mobile or airborne platform housing the ORSI, or the one or more targets. For example, if the ORSI is mounted on a helicopter, it may be difficult to aim exactly at a target due to the helicopter movements. As such, it may be desirable in some situations to have a larger retroreflector target to aim at, yet without a very large number of corner cube reflectors that can be costly and add unnecessary weight. A composite retroreflector could be useful in this situation. A composite retroreflector could consist of high reflectivity corner cube retroreflectors dispersed in a background of thin, light-weight retroreflector material (such as retroreflective tape or paint) such that if the measurement beam wanders, it will be reflected by both the tape and corner cube retroreflector.

A bundled ORSI head utilizing a multiplexed ORSI, for example, as described in U.S. Pat. No. 5,748,325 may be used. A bundled ORSI head may comprise two or more transmitter/receivers or, alternatively, multiple transmitters and a single receiver. Each transmitter may be activated sequentially such that each round of measurement is accomplished before a second combination of transmitter and detector are activated. The measurement beam path of each transmitter may be parallel, or substantially parallel, to the measurement beam path of the one or more other transmitters. In some embodiments, one measurement beam path may have a slight angle relative to a second measurement beam path; the angle is of a magnitude such that when the bundled ORSI head is aimed at a target, and either the ORSI, or the target, or both the ORSI and the target are moving, at least one measurement beam is reflected off the target and back to the receiver.

One, or more than one, measurement may be taken from each target.

Figure 7:
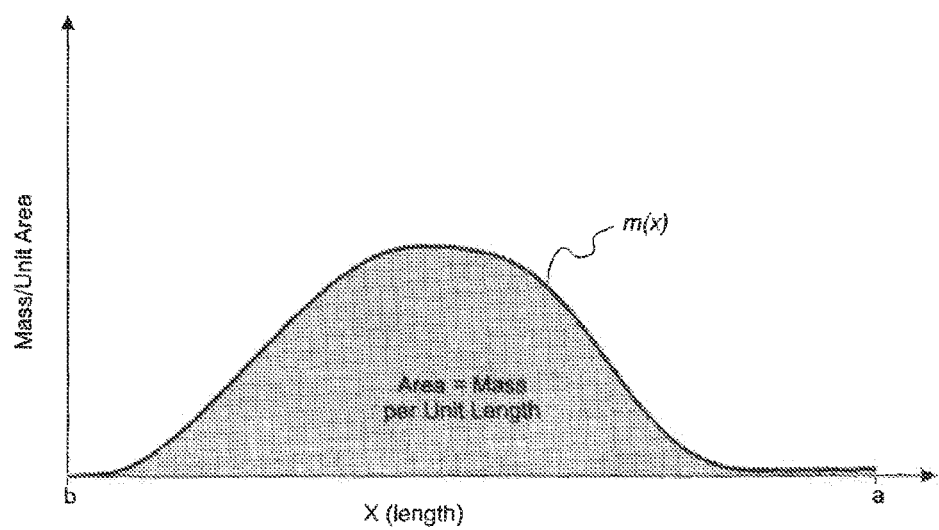
FIG. 7 shows a graph of the mass of pollutant through a cross section of a plume. In this illustration, the measurement beam paths are in a vertical (z) direction, in units of mass per unit area versus length along the x axis. The area under the curve m(x) is the mass of airborne matter per unit length.

Each ORSI measurement along a measurement beam path (expressed as ppm-m or mass per unit area), and adjusted for the background concentration of the airborne matter, can be plotted for each position on a graph (for example as shown in FIGS. 4 and 8). For example, in a rectangular coordinate system with the x-axis in a cross-wind horizontal direction, y is in the direction of the wind, and z is in the vertical direction. An ORSI measurement beam path may be in the vertical (z) direction. A plurality of measurement beam paths in the x-z plane provide a measurement surface. Coordinates a and b (FIG. 7) along the x axis are the end points of the measurement surface and bracket or substantially bracket the emission plume to be measured. The data can then be plotted as ORSI measurement values for a given location within the measurement surface (x-axis). The measurement points (representing each measurement beam path) on the graph can be joined linearly, curvi-linearly, or by regression or any manner of interpolation and integrated. The resulting curve can be represented by the function m(x) as shown generally in FIG. 7. The representative wind velocity for each position on the x axis can be written u(x). The flux of emissions M, as mass per unit time, can be written:

$$M \stackrel{a}{=}_b \int m(x)u(x)dx$$

The more measurement paths available to define m(x) or u(x), the better is the accuracy. As such, the invention is not limited as to the number of measurement paths used. If the site is sufficiently small such that u(x) can be represented by a single average value $\overline{U}$, than:

$$M \stackrel{a}{=}_b \overline{U} \int m(x)dx$$

Similar equations can be developed if the ORSI measurement beam path is in the horizontal (x) direction, with the measurement plane in the x-z plane.

Similar equations can be developed if the x-y-z coordinate system is rotated, as may be useful for example if the ground surface is sloped.

Mass includes weight, since weight is the product of mass and acceleration due to gravity.

If the surface, or portion thereof, formed by the measurement beam paths is not perpendicular to the wind direction, then each measurement value determined along a beam path (path-integrated concentration in ppm-m or mass per unit area) can be projected in the wind direction onto an imaginary plane (a measurement plane) that is oriented perpendicular to the wind direction, and then the above two equations can be applied. However, these equations do not have a y variable and thus the construction of this measurement plane, while useful for visualization and presentation of the data, is not necessary for the application of the method.

The software comprises statements and instructions for obtaining a fugitive emission flux measurement of airborne matter at a site, and correcting the measurements for the background concentration of airborne matter. The wind velocity, distance of the ORSI from the target, travel or flight path length, fugitive emission integrated concentration and the background concentration of airborne matter may be obtained as described herein. The resulting fugitive emission flux measurement, or net emission flux measurement may be stored on a computer readable memory for later access or manipulation. Alternatively and as demonstrated by FIG. 4, the fugitive emission flux can be calculated by hand.

Therefore, some embodiments of the invention provide for a method for obtaining a fugitive emission flux measurement of airborne matter at a site, comprising the steps of (a) selecting one or more than one measurement surface, the one or more measurement surfaces being along a transverse straight line, or along a curved path, relative to the wind direction; (b) obtaining a wind velocity at or near each of the one or more than one measurement surface; (c) measuring a mass per unit area of the airborne matter at one or more than one measurement path along the one or more than one measurement surface; (d) calculating the total airborne matter mass per unit length for the one or more than one measurement surface; (e) determining the emission flux of the airborne matter in mass per unit time using the mass per unit length of the airborne matter of the one or more than one measurement surface and the wind velocity.

The present invention will be further illustrated in the following example. However it is to be understood that these examples are for illustrative purposes only, and should not be used to limit the scope of the present invention in any manner.

Example 1

Measuring and Determining Flux of a Fugitive Emission Plume

A controlled methane (subject gas) leak is illustrated in FIG. 3 as a fugitive emission plume of varying integrated concentrations with distance from the source, after having subtracted the background concentration. The leak has a flow rate of 17 SCFM (standard cubic feet/minute; one SCFM is equal to 1.7 m³/hour). Three measurement surfaces (A, B, C) as illustrated were obtained using an airborne ORSI (DIAL using ND:YLF lasers) approximately at 300 m above the ground surface. In this special case, the ORSI was able to obtain measurements up to approximately 19 m on either side of a flight path that was parallel to the wind direction.

In this example, the wind speed is 1.3 meters per second.

The mass of methane per unit length for the three measurement surfaces A, B, C is provided in Table 1. The mass per unit length for each of the measurement surfaces is calculated by measuring the area under the ppm-m versus length curve (FIG. 4) and converting the ppm-m² value by the conversion factor for methane of 1 ppm equals about 0.68 milligrams per cubic meter.

TABLE 1

| Surface | mass per unit length (grams/m) | calculated emission flux (grams/second) |
|---|---|---|
| A | 3.8 | 4.9 |
| B | 4.6 | 6.0 |
| C | 4.3 | 5.6 |

By comparison, the controlled release rate of methane in grams per second may be determined from the density of the subject gas (methane has a density of about 0.68 kg/m³):

$$\text{Flux} = 17 SCFM \times 1.7 \text{ m}^3/\text{hours}/scfm \times 0.68 \text{ kg/m}^3$$

$$= 19.7 \text{ kg/hr } (\sim 5.5 \text{ grams/second})$$

Example 2

Adjusting an ORSI Measurement within an Emission Plume for Uniform Background Concentration Measurement in the background region records the following data:
Distance between ORSI and target=224 m
ORSI measurement=380.8 ppm-m
Therefore, background concentration of methane=380.8 ppm-m/224 m=1.7 ppm.

Measurement in the fugitive emission plume records the following data:
Distance between the ORSI and target=305 m
ORSI measurement=931 ppm-m
Therefore, the portion of the ORSI integrated concentration measurement due to background=1.7 ppm×305 m=518.5 ppm-m
The portion of the ORSI integrated concentration measurement due to the fugitive emission (measurement after subtracting background concentration)=931 ppm-m−518.5 ppm-m=412.5 ppm-m

REFERENCES

Scharff, H., "Landfill Gas Production and Emission on Former Landfill", Interreg IIIC report (on the internet), October, 2005

Lamb, B., et. al., "Development of Atmospheric Tracer Methods to Measure Methane Emissions from Natural Gas Facilities and Urban Areas", Environmental Science & Technology, Vol. 29, pp 1468-1479, 1995.

Czepiel, et. al, "Landfill methane emissions measured by enclosure and atmospheric tracer methods", Journal of Geophysical Research, Vol. 101, No. D11, 1996.

Mount, G. et. al, "DOAS Measurement of Atmospheric Ammonia Emissions at a Dairy", 10th Annual Emission Inventory Conference, EPA, 2001.

Griffith, D., et. al., "Methane Emissions from Free-Ranging Cattle: Comparison of Tracer and Integrated Horizontal Flux Techniques", Journal of Environmental Quality, Vol 37, Issue 2, 582-591, March/April 2008.

Hensen, A., & Scharff, H., "Methane Emission Estimates from Landfills Obtained with Dynamic Plume Measurements", Water, Air and Soil Pollution: Focus, Vol. 1, No. 5-6, 455-464(10), 2001.

Huitric, R. L., and Kong, D., "Measuring Landfill Gas Collection Efficiency Using Surface Methane Concentrations", SWANA 29$^{th}$ Annual LFG Symposium, St. Petersburg, Fla., Mar. 27-30, 2006.

Thoma, E., et. al, "Development of EPA OTM 10 for Landfill Applications Interim Report 2", Global Waste Management Symposium, Colorado, USA, Sep. 7-10, 2008.

Tregoures, A., et. al., "Comparison of seven methods for measuring methane flux at a municipal solid waste landfill site", Waste Management & Research, 17: pp 453-458, 1999.

Laubach, J., and Kelliher, F., "Methane emissions from dairy cows: Comparing open-path laser measurements to profile-based techniques", Agricultural and Forest Meteorology, 135, pp 340-345, 2005.

Weibring, P. et. al, "Remote monitoring of industrial emissions by combination of lidar and plume velocity measurements", Applied Physics B Lasers and Optics, 66, 383-388, 1998.

Chambers, A., "Optical Measurement Technology for Fugitive Emissions from Upstream Oil and Gas Facilities", report prepared by Alberta Research Council Inc., Dec. 15, 2004.

Chambers, A., et. al, "DIAL Measurements of Fugitive Emissions from Natural Gas Plants and the Comparison with Emission Factor Estimates", 15$^{th}$ International Emission Inventory Conference, New Orleans, May 15-18, 2006.

System and Method for Remote Quantitative Detection of Fluid Leaks from Natural Gas or Oil Pipeline, U.S. Pat. Nos. 6,822,742 and 6,995,846.

United States Environmental Protection Agency, "Other Method 10 (OTM 10)—Optical Remote Sensing for Emission Characterization from Non-point Sources", Jun. 14, 2006.

Babilott, A. et. al, "Fugitive methane emissions from landfills: A field comparison of five methods on a French landfill", Global Waste Management Symposium, Colorado, USA, Sep. 7-10, 2008.

All citations are herein incorporated by reference.

One or more currently preferred embodiments have been described by way of example. It will be apparent to persons skilled in the art that a number of variations and modifications can be made without departing from the scope of the invention as defined in the claims.

What is claimed is:

1. A method of obtaining a fugitive emission flux measurement of airborne matter within a fugitive emission from an emission source of interest, comprising:
   a) measuring the airborne matter using an airborne platform comprising an optical remote sensing instrument (ORSI) and one or more than one ground-based target along one or more than one measurement surface using two or more than two measurement beam paths, where each of the two or more than two measurement beam paths are vertical or substantially vertical, and parallel to each other, or substantially parallel to each other, the one or more than one measurement surface is of a height and width that spans or substantially spans the fugitive emission, and is oriented along a transverse straight path, or along a curved path, relative to a wind direction, and determining a parts per million meter (ppm-m) or a mass per unit area measurement of the airborne matter for each of the two or more than two measurement beam paths, the height being a distance between the airborne platform and the ground-based target;
   b) determining a wind velocity at one or more locations at or near each of the one or more than one measurement surface to obtain a representative wind velocity;
   c) integrating, with respect to a horizontal, or substantially horizontal, length along the one or more than one measurement surface that is perpendicular to the wind direction and transverse to a direction of the two or more than two measurement beam paths, the parts per million meter (ppm-m) or mass per unit area measurement of the airborne matter obtained from each of the two or more than two measurement beam paths, and determining a total mass per unit length of the airborne matter for each of the one or more than one measurement surface; and
   d) calculating the fugitive emission flux of the airborne matter in mass per unit time using a total mass per unit length of the airborne matter and the representative wind velocity.

2. The method of claim 1, comprising a step of correcting for a background concentration of airborne matter or an upwind emission source, by:
   determining the background concentration and using this measurement and the measurement of airborne matter from each of the two or more than two beam paths, to obtain a corrected measurement of the airborne matter as measured in step (a), or
   correcting the fugitive emission flux determined in (d) by using steps (a) to (d) to determine a flux of airborne matter upwind of the emission source of interest.

3. The method of claim 1 wherein the airborne matter in step (a) is measured using an optical remote sensing method selected from: tunable diode laser (TDL) absorption spectroscopy, differential absorption laser detection and ranging (DIAL), open path Fourier transform infrared (OP-FTIR) spectroscopy, differential optical absorption spectroscopy (DOAS), Raman spectroscopy, or backscatter absorption gas imaging (BAGI).

4. The method of claim 1 wherein the wind velocity in step (b) is obtained with an anemometer or sodar.

5. The method of claim 1 wherein in step (a), a length of the two or more than two measurement beam paths are measured.

6. The method of claim 1, wherein the ground-based target is the ground, a surface of the emission source or a reflector mounted on the ground, a ground-based vehicle, or the surface of the emission source.

7. The method of claim 1, wherein the amount of airborne matter along a top of the measurement surface is measured.

8. A computer readable memory having recorded thereon statements and instructions for execution by a computer to carry out the method of claim 1, wherein the computer readable memory is non-transitory.

9. A method of obtaining a fugitive emission flux measurement of airborne matter within a fugitive emission from an emission source of interest, comprising:
   a) measuring the airborne matter using a ground-based platform comprising an optical remote sensing instrument (ORSI) and an airborne target along one or more than one measurement surface using two or more than two measurement beam paths, where each of the two or more than two measurement beam paths are vertical or substantially vertical, and parallel to each other, or substantially parallel to each other, the one or more than one measurement surface is of a height and width that spans or substantially spans the fugitive emission, and is oriented along a transverse straight path, or along a curved path, relative to a wind direction, and determining a parts per million meter (ppm-m) or a mass per unit area measurement of the airborne matter for each of the two or more than two measurement beam paths, the height being the distance between the ground-based platform and the airborne target;
b) determining a wind velocity at one or more locations at or near each of the one or more than one measurement surface to obtain a representative wind velocity;
c) integrating, with respect to a horizontal, or substantially horizontal, length along the measurement surface that is perpendicular to the wind direction and transverse to a direction of the two or more than two measurement beam paths, the parts per million meter (ppm-m) or mass per unit area measurement of the airborne matter obtained from each of the two or more than two measurement beam paths, and determining a total mass per unit length of the airborne matter for each of the one or more than one measurement surface; and
d) calculating the fugitive emission flux of the airborne matter in mass per unit time using a total mass per unit length of the airborne matter and the representative wind velocity.

10. The method of claim 9, comprising a step of correcting for a background concentration of airborne matter or an upwind emission source, by:

determining the background concentration and using this measurement and the measurement of airborne matter from each of the two or more than two beam paths, to obtain a corrected measurement of the airborne matter as measured in step (a), or correcting the fugitive emission flux determined in (d) by using steps (a) to (d) to determine a flux of airborne matter upwind of the emission source of interest.

11. The method of claim 9, wherein the airborne matter in step (a) is measured using an optical remote sensing method selected from: tunable diode laser (TDL) absorption spectroscopy, differential absorption laser detection and ranging (DIAL), open path Fourier transform infrared (OP-FTIR) spectroscopy, differential optical absorption spectroscopy (DOAS), Raman spectroscopy, or backscatter absorption gas imaging (BAGI).

12. The method of claim 9, wherein the wind velocity in step (b) is obtained with an anemometer or sodar.

13. The method of claim 9 wherein in step (a), a length of the two or more than two measurement beam paths are measured.

14. The method of claim 9, wherein the airborne target is one or more reflectors mounted on an airborne platform, or the surface of the airborne platform.

15. The method of claim 9, wherein the amount of airborne matter along a top of the measurement surface is measured.

16. A computer readable memory having recorded thereon statements and instructions for execution by a computer to carry out the method of claim 9, wherein the computer readable memory is non-transitory.

* * * * *

UNITED STATES PATENT AND TRADEMARK OFFICE
CERTIFICATE OF CORRECTION

PATENT NO. : 8,781,755 B2
APPLICATION NO. : 12/964149
DATED : July 15, 2014
INVENTOR(S) : Colin Irving Wong It is certified that error appears in the above-identified patent and that said Letters Patent is hereby corrected as shown below:

In the Specification

In column 8, line 59, delete "per unit are" and insert --per unit area--.

In column 14, line 45, delete the formula and replace with the following:

$$M = \int_{b}^{a} m(x)\, u(x)\, dx$$

In column 14, line 55, delete the formula and replace with the following:

$$M = \bar{U} \int_{b}^{a} m(x)\, dx$$

Signed and Sealed this
Thirty-first Day of March, 2015

Michelle K. Lee
*Director of the United States Patent and Trademark Office*